US011370856B2

(12) United States Patent
Nam et al.

(10) Patent No.: US 11,370,856 B2
(45) Date of Patent: Jun. 28, 2022

(54) SUPER ABSORBENT POLYMER AND PREPARATION METHOD FOR THE SAME

(71) Applicant: LG Chem, Ltd., Seoul (KR)

(72) Inventors: Dae Woo Nam, Daejeon (KR); Ki Hyun Kim, Daejeon (KR); Jun Kyu Kim, Daejeon (KR); Young Jae Hur, Daejeon (KR)

(73) Assignee: LG Chem, Ltd.

( * ) Notice: Subject to any disclaimer, the term of this patent is extended or adjusted under 35 U.S.C. 154(b) by 138 days.

(21) Appl. No.: 17/041,227

(22) PCT Filed: Mar. 20, 2019

(86) PCT No.: PCT/KR2019/003246
§ 371 (c)(1),
(2) Date: Sep. 24, 2020

(87) PCT Pub. No.: WO2019/190120
PCT Pub. Date: Oct. 3, 2019

(65) Prior Publication Data
US 2021/0009725 A1 Jan. 14, 2021

(30) Foreign Application Priority Data

Mar. 30, 2018 (KR) .................... 10-2018-0037268
Mar. 19, 2019 (KR) .................... 10-2019-0031083

(51) Int. Cl.
| | | |
|---|---|---|
| *C08F 220/06* | (2006.01) | |
| *A61L 15/24* | (2006.01) | |
| *C08F 20/06* | (2006.01) | |
| *C08J 3/12* | (2006.01) | |
| *C08J 3/24* | (2006.01) | |
| *C08K 3/36* | (2006.01) | |
| *C08F 222/10* | (2006.01) | |

(52) U.S. Cl.
CPC ............... *C08F 20/06* (2013.01); *C08J 3/12* (2013.01); *C08J 3/24* (2013.01); *A61L 15/24* (2013.01); *C08F 220/06* (2013.01); *C08F 222/102* (2020.02); *C08F 222/103* (2020.02); *C08F 222/104* (2020.02); *C08F 222/105* (2020.02); *C08F 222/1006* (2013.01); *C08J 2433/08* (2013.01); *C08K 3/36* (2013.01)

(58) Field of Classification Search
None
See application file for complete search history.

(56) References Cited

U.S. PATENT DOCUMENTS

| | | | |
|---|---|---|---|
| 4,883,478 A | 11/1989 | Lerailler et al. | |
| 5,624,967 A * | 4/1997 | Hitomi ............... | A61L 15/24 521/64 |
| 2010/0041824 A1 | 2/2010 | Torii et al. | |
| 2011/0059329 A1 | 3/2011 | Dobrawa et al. | |
| 2011/0224361 A1 | 9/2011 | Daniel et al. | |
| 2011/0301560 A1 * | 12/2011 | Fujimura .............. | C08J 3/12 525/384 |
| 2012/0037847 A1 | 2/2012 | Torii et al. | |
| 2014/0193641 A1 | 7/2014 | Torii et al. | |
| 2017/0216817 A1 | 8/2017 | Torii et al. | |
| 2018/0243464 A1 | 8/2018 | Hwang et al. | |
| 2018/0244868 A1 | 8/2018 | Lee et al. | |
| 2018/0312645 A1 | 11/2018 | Lee et al. | |

FOREIGN PATENT DOCUMENTS

| | | |
|---|---|---|
| CN | 102597010 A | 7/2012 |
| EP | 0686650 A1 | 12/1995 |
| EP | 2377897 A1 | 10/2011 |
| EP | 2727953 A1 | 5/2014 |
| EP | 3202823 A1 | 8/2017 |
| EP | 3336134 A1 | 6/2018 |
| JP | 2005021704 A | 1/2005 |
| JP | 2009051952 A | 3/2009 |
| JP | 2010521537 A | 6/2010 |
| KR | 20110114535 A | 10/2011 |
| KR | 20160117180 A | 10/2016 |
| KR | 20170106111 A | 9/2017 |
| KR | 20170111295 A | 10/2017 |
| KR | 20170112856 A | 10/2017 |
| WO | 8703208 A1 | 6/1987 |
| WO | 2010073658 A1 | 7/2010 |
| WO | 2016159600 A1 | 10/2016 |

OTHER PUBLICATIONS

Extended European Search Report for Application No. 19775486.4, dated Mar. 19, 2021, 14 pages.
International Search Report for Application No. PCT/KR2019/003246, dated Jul. 3, 2019, pp. 1-3.
Odian, Principles of Polymerization, Second Edition, 1981, p. 203, Wiley.
Schwalm, UV Coatings Basics, Recent Developments and New Applications, Dec. 2006, p. 115, Elsevier Science.

* cited by examiner

*Primary Examiner* — Richard A Huhn
(74) *Attorney, Agent, or Firm* — Lerner, David, Littenberg, Krumholz & Mentlik, LLP

(57) ABSTRACT

The present invention relates to super absorbent polymer and a method for preparing the same. According to the super absorbent polymer and preparation method for the same of the present invention, super absorbent polymer having improved rewet property and vortex time can be provided.

20 Claims, No Drawings

SUPER ABSORBENT POLYMER AND PREPARATION METHOD FOR THE SAME

CROSS-REFERENCE TO RELATED APPLICATIONS

The present application is a national phase entry under 35 U.S.C. § 371 of International Application No. PCT/KR2019/003246, filed on Mar. 20, 2019, which claims priority from Korean Patent Application No. 10-2018-0037268, filed on Mar. 30, 2018, and Korean Patent Application No. 10-2019-0031083, filed on Mar. 19, 2019, the disclosures of which are herein incorporated by reference in their entirety.

BACKGROUND OF THE INVENTION

(a) Field of the Invention

The present invention relates to super absorbent polymer and a method for preparing the same. More specifically, the present invention relates to super absorbent polymer having improved rewet property and vortex time, and a method for preparing the same.

(b) Description of the Related Art

Super absorbent polymer (SAP) is synthetic polymer material that can absorb moisture of 500 to 1000 times of self-weight, and is also named differently as super absorbency material (SAM), absorbent gel material (AGM), etc. according to developing companies. The super absorbent polymer began to be commercialized as sanitary items, and currently, it is being widely used as hygienic goods such as a disposable diaper and the like, water-holding material for soil, water stop material for civil engineering and architecture, sheets for raising seedling, freshness preservatives in the field of food circulation, fomentation material, and the like.

In most cases, such super absorbent polymer is being widely used in the field of hygienic goods such as a diaper or sanitary pad, etc., and for such use, it is required to exhibit high absorption power to moisture, and the like, and the absorbed moisture should not escape even under external pressure, and besides, it should properly maintain the shape even when it absorbs water and the volume is expanded (swollen), thus exhibiting excellent permeability.

However, it is known that centrifuge retention capacity (CRC) indicating the basic absorption power and water retention power of super absorbent polymer, and absorption under load (AUL) indicating the property of retaining absorbed moisture despite the external pressure are difficult to be simultaneously improved. In case the whole crosslinking density of super absorbent polymer is controlled low, centrifuge retention capacity may become relatively high, but the crosslink structure may become loose, and gel strength may decrease, thus deteriorating absorption under pressure. To the contrary, in case the crosslinking density is controlled high to improve absorption under pressure, it may become difficult to absorb moisture between the dense crosslink structures, thus deteriorating centrifuge retention capacity. For these reasons, there is a limit in providing super absorbent polymer having simultaneously improved centrifuge retention capacity and absorption under pressure.

However, with the recent thinning of hygienic goods such as diapers and sanitary pads, super absorbent polymer is required to have higher absorption performances. Among them, it is an important problem to simultaneously improve the conflicting properties of centrifuge retention capacity and absorption under pressure, and improve permeability, and the like.

And, to the hygienic goods such as diapers or sanitary pads, and the like, pressure may be applied by the weight of a user. Particularly, if super absorbent polymer applied for a diaper or a sanitary pad absorbs liquid, and then, a pressure is applied by the weight of a user, rewet phenomenon wherein a part of the liquid absorbed in the super absorbent polymer exudes again, and urine leakage may be generated.

Thus, many attempts are being made to inhibit such a rewet phenomenon. However, a specific method of effectively inhibiting rewet phenomenon has not been suggested yet.

SUMMARY OF THE INVENTION

In order to solve the problem of the prior art, it is an object of the present invention to provide super absorbent polymer in which rewet and urine leakage are inhibited, and a method for preparing the same.

In order to achieve the objects, one aspect of the present invention provides super absorbent polymer comprising:

base resin in which acrylic acid-based monomers having acid groups, of which at least a part are neutralized, and an internal cross-linking agent are cross-linked;

a surface modification layer formed on the surface of the base resin particles, in which the cross-linked polymer is additionally cross-linked by an epoxy-based surface cross-linking agent; and inorganic filler, wherein the internal cross-linking agent comprises a poly(meth)acrylate-based first internal cross-linking agent:a polyol polyglycidyl ether-based second internal cross-linking agent at a weight ratio of 1:40 to 1:1200, and the surface modification layer includes hydrophobic material having a melting temperature (Tm) of 40 to 80° C., and water solubility at 25° C. of 70 mg/L or less.

And, another aspect of the present invention provides a method for preparing super absorbent polymer comprising steps of:

preparing base resin in which acrylic acid-based monomers having acid groups, of which at least a part are neutralized, and an internal cross-linking agent are cross-linked (step 1);

mixing hydrophobic material having a melting temperature (Tm) of 40 to 80° C., and water solubility at 25° C. of 70 mg/L or less, and an epoxy-based surface cross-linking agent with the base resin (step 2); and increasing the temperature of the mixture of step 2 to conduct surface modification of the base resin (step 3), wherein the internal cross-linking agent comprises a poly(meth)acrylate-based first internal cross-linking agent:a polyol polyglycidyl ether-based second internal cross-linking agent at a weight ratio of 1:40 to 1:1200, and inorganic filler is additionally mixed with the base resin in the step 2, or inorganic filler is mixed with the super absorbent polymer passing through the step 3.

According to the super absorbent polymer and preparation method for the same of the present invention, super absorbent polymer exhibiting excellent absorption properties, in which rewet and urine leakage are inhibited, can be provided.

DETAILED DESCRIPTION OF THE EMBODIMENTS

Although various modifications can be made to the present invention and the present invention may have various forms, specific examples will be illustrated and explained in detail below. However, it should be understood that these are not intended to limit the present invention to specific disclosure, and that the present invention includes all the modifications, equivalents or replacements thereof without departing from the spirit and technical scope of the invention.

Hereinafter, a method for preparing super absorbent polymer composition according to specific embodiments of the present invention will be explained in more detail.

Super absorbent polymer according to one embodiment of the present invention comprises:

base resin in which acrylic acid-based monomers having acid groups, of which at least a part are neutralized, and an internal cross-linking agent are cross-linked;

a surface modification layer formed on the surface of the base resin particles, in which the cross-linked polymer is additionally cross-linked by an epoxy-based surface cross-linking agent; and inorganic filler, wherein the internal cross-linking agent comprises a poly(meth)acrylate-based first internal cross-linking agent:a polyol polyglycidyl ether-based second internal cross-linking agent at a weight ratio of 1:40 to 1:1200, and the surface modification layer includes hydrophobic material having a melting temperature (Tm) of 40 to 80° C., and water solubility at 25° C. of 70 mg/L or less.

And, a hygienic product according to another embodiment of the present invention comprises the above described super absorbent polymer.

And, a method for preparing super absorbent polymer according to another embodiment of the present invention comprises steps of:

preparing base resin in which acrylic acid-based monomers having acid groups, of which at least a part are neutralized, and an internal cross-linking agent are cross-linked (step 1);

mixing hydrophobic material having a melting temperature (Tm) of 40 to 80° C., and water solubility at 25° C. of 70 mg/L or less, and an epoxy-based surface cross-linking agent with the base resin (step 2); and increasing the temperature of the mixture of step 2 to conduct surface modification of the base resin (step 3), wherein the internal cross-linking agent comprises a poly(meth)acrylate-based first internal cross-linking agent:a polyol polyglycidyl ether-based second internal cross-linking agent at a weight ratio of 1:40 to 1:1200, and inorganic filler is additionally mixed with the base resin in the step 2, or inorganic filler is mixed with the super absorbent polymer passing through the step 3.

Throughout the specification, "base resin" or "base resin powder" means polymer of water soluble ethylenically unsaturated monomers, made in the form of particles or powder by drying and grinding, and which is not subjected to a surface modification or surface crosslinking step described below.

The hydrogel polymer obtained by the polymerization reaction of acrylic acid-based monomers may be subjected to the processes of drying, grinding, sieving, surface cross-linking, and the like, and commercialized as a powder super absorbent polymer product.

Recently, a period during which surface dryness can be maintained when diapers are practically used, as well as absorption properties of super absorbent polymer such as centrifuge retention capacity, permeability, and the like, is becoming an important measure for estimating the properties of diapers.

It was confirmed that the super absorbent polymer obtained by the preparation method of one embodiment has excellent centrifuge retention capacity, absorption under pressure, permeability, and the like, thus exhibiting excellent absorption performance, maintains dryness even after swollen by brine, and can effectively prevent rewet and urine leakage.

In the preparation method of super absorbent polymer of the present invention, the raw material of the super absorbent polymer, namely, the monomer composition comprising acrylic acid-based monomers having acid groups, of which at least a part are neutralized, an internal crosslinking agent, and a polymerization initiator is polymerized to obtain hydrogel polymer, and dried, ground and sieved to prepare base resin (step 1).

Hereinafter, it will be explained in more detail.

The monomer composition, which is the raw material of the super absorbent polymer, comprises acrylic acid-based monomers having acid groups, of which at least a part are neutralized, and a polymerization initiator.

The acrylic acid-based monomer is a compound represented by the following Chemical Formula 1:

 [Chemical Formula 1]

In the Chemical Formula 1, $R_1$ is a C2-5 alkyl group comprising an unsaturated bond, $M^1$ is a hydrogen atom, a monovalent or divalent metal, an ammonium group or an organic amine salt.

Preferably, the acrylic acid-based monomers may be one or more selected from the group consisting of acrylic acid, methacrylic acid, and monovalent metal salts, divalent metal salt, ammonium salts and organic amine salts of these acids.

Here, the acrylic acid-based monomers may have acid groups, and at least a part of the acid groups may be neutralized. Preferably, monomers that are partially neutralized with alkali substance such as sodium hydroxide, potassium hydroxide, ammonium hydroxide, etc. may be used. Here, the neutralization degree of the acrylic acid-based monomers may be 40 to 95 mol %, or 40 to 80 mol %, or 45 to 75 mol %. Although the range of the neutralization degree may vary according to the final properties, if the neutralization degree is too high, neutralized monomers may be precipitated, thus rendering smooth progression of polymerization difficult, and to the contrary, if the neutralization degree is too low, the absorption power of the polymer may be significantly lowered, and the polymer may exhibit rubber-like property, which is difficult to handle.

The concentration of the acrylic acid-based monomers may be about 20 to about 60 wt %, preferably about 40 to about 50 wt %, based on the monomer composition comprising the raw materials of super absorbent polymer and solvents, and it may be controlled to an appropriate concentration considering a polymerization time and reaction conditions, and the like. However, if the concentration of the monomers becomes too low, the yield of super absorbent polymer may decrease and economic efficiency may be lowered, and if it becomes too high, process problems may be generated such as precipitation of a part of the monomers or low grinding efficiency during grinding of the polymerized hydrogel polymer, and the properties of super absorbent polymer may be deteriorated.

A polymerization initiator that is used in the preparation method of super absorbent polymer is not specifically limited as long as it is commonly used for the preparation of super absorbent polymer.

Specifically, as the polymerization initiator, a thermal polymerization initiator or a photopolymerization initiator by UV irradiation may be used according to a polymerization method. However, even in the case of photopolymerization, since a certain amount of heat is generated by UV irradiation, etc., and heat is generated to some degree according to the progression of an exothermic polymerization reaction, a thermal polymerization initiator may be additionally included.

The photopolymerization initiator is not limited in terms of its construction, as long as it is a compound capable of forming a radical by light such as UV.

As the photopolymerization initiator, one or more selected from the group consisting of benzoin ether, dialkyl acetophenone, hydroxyl alkylketone, phenyl glyoxylate, benzyl dimethyl Ketal, acyl phosphine, and α-aminoketone may be used. Among them, as the acyl phosphine, commercially available lucirin TPO, i.e., 2,4,6-trimethyl-benzoyl-trimethyl phosphine oxide may be used. More various photopolymerization initiators are described in Reinhold Schwalm, "UV Coatings: Basics, Recent Developments and New Application (Elsevier 2007)", page 115, and are not limited to the above described examples.

The photopolymerization initiator may be included in the concentration of about 0.01 to about 1.0 wt %, based on the monomer composition. If the concentration of the photopolymerization initiator is too low, polymerization speed may become slow, and if it is too high, the molecular weight of super absorbent polymer may be small and the properties may become irregular.

And, as the thermal polymerization initiator, at least one selected from the group consisting of a persulfate initiator, an azo initiator, hydrogen peroxide, and ascorbic acid may be used. Specific examples of the persulfate initiator may include sodium persulfate ($Na_2S_2O_8$), potassium persulfate ($K_2S_2O_8$), ammonium persulfate (($NH_4)_2S_2O_8$), etc., and, specific examples of the azo initiator may include 2,2-azobis (2-amidinopropane)dihydrochloride, 2,2-azobis-(N,N-dimethylene)isobutyramidinedihydrochloride, 2-(carbamoylazo)isobutyronitril, 2,2-azobis[2-(2-imidazolin-2-yl) propane]dihydrochloride, 4,4-azobis-(4-cyanovalericacid), etc. More various thermal initiators are described in "Principle of Polymerization (Wiley, 1981)", Odian, page 203, and are not limited to the above described examples.

According to one embodiment of the invention, the monomer composition may further comprise an internal cross-linking agent as the raw material of super absorbent polymer. Such an internal cross-linking agent is used to crosslink the inside of polymer of acrylic acid-based monomers, i.e., base resin, and is distinguished from a surface cross-linking agent for cross-linking the surface of the polymer.

Particularly, in the preparation method of one embodiment of the present invention, the poly(meth)acrylate-based first internal cross-linking agent and the polyol polyglycidyl ether-based second internal cross-linking agent are used in combination, and the first internal cross-linking agent:the second internal cross-linking agent may be used at a weight ratio of 1:40 to 1:1200. More specifically, the weight ratio of the first internal cross-linking agent:the second internal cross-linking agent may be 1:40 or more, or 1:50 or more, or 1:100 or more, or 1:120 or more, or 1:125 or more, or 1:300 or more, or 1:350 or more, and 1:1200 or less, or 1:1000 or less, or 1:800 or less, or 1:600 or less, or 1:500 or less.

Thereby, while maintaining excellent basic absorption properties of the prepared super absorbent polymer, for example, centrifuge retention capacity, absorption under pressure, and absorption speed, rewet property may be further improved. If the weight ratio of the first and second internal cross-linking agents does not fall within the above range, basic absorption properties may be deteriorated, or rewet property may not be improved. And, during polymerization, volume expansion may excessively occur, rendering the polymerization process unstable.

As the first internal cross-linking agent, polyol poly(meth) acrylate-based compound, for example, C2-10 polyol poly (meth)acrylate-based compounds may be used, and more specific examples thereof may include one or more selected from the group consisting of trimethylolpropane tri(meth) acrylate, ethyleneglycol di(meth)acrylate, polyethyleneglycol di(meth)acrylate, propyleneglycol di(meth)acrylate, polypropyleneglycol di(meth)acrylate, butanedioldi(meth) acrylate, butyleneglycoldi(meth)acrylate, diethyleneglycol di(meth)acrylate, hexanediol di(meth)acrylate, triethyleneglycol di(meth)acrylate, tripropyleneglycol di(meth) acrylate, tetraethyleneglycol di(meth)acrylate, dipentaerythritol pentaacrylate, glycerin tri(meth)acrylate, and pentaerythritol tetraacrylate.

And, as the second internal cross-linking agent, polyol polyglycidyl ether compounds having multifunctional epoxy groups, for example, C2-10 polyol polyglycidyl ether compounds may be used, and specific examples thereof may include multivalent epoxy-based compounds such as ethyleneglycol diglycidyl ether, polyethyleneglycol diglycidyl ether, glycerol polyglycidyl ether, propyleneglycol diglycidyl ether, and polypropyleneglycol diglycidyl ether.

By the combined use of these specific internal cross-linking agents, the internal crosslink structure of the super absorbent polymer may be further optimized, thereby further improving permeability and rewet property, while maintaining excellent absorption properties.

The sum of the first and second internal cross-linking agents may be about 0.01 to about 0.5 parts by weight, based on 100 parts by weight of the acrylic acid-based monomers.

According to one embodiment of the invention, the monomer composition may further comprise colloidal silica.

The colloidal silica means silica wherein silica particles are stably dispersed in water without precipitation or aggregation, and at least a part of the surfaces of the silica particles are ionized. The preparation method of the colloidal silica is not specifically limited, and any known methods such as electrodialysis, a sol-gel process, an ion exchange process, an acid neutralization process, and the like may be used.

The particle diameter of the colloidal silica is preferably about 5 nm or more, or about 10 nm or more, and about 100 nm or less, or about 50 nm or less, or about 30 nm or less. If the particle diameter of the colloidal silica is too small, production cost may increase due to expensive cost, and if it is too large, the effect of rewet improvement may not be obtained.

And, the colloidal silica may be added in the concentration of about 0.01 to about 1.0 part by weight, or about 0.02 to about 0.5 parts by weight, based on 100 parts by weight of the acrylic acid-based monomers. If the amount of the colloidal silica used is greater than 1.0 part by weight, centrifuge retention capacity of super absorbent polymer may be deteriorated, and if it is less than 0.01 parts by weight, rewet improvement effect may not be obtained, and thus, the above range may be preferable.

And, if the colloidal silica fails to maintain a colloidal state and is precipitated in a monomer composition, rewet improvement effect may not be obtained, and thus, it is preferable to use colloidal silica that maintains a stable colloidal state in a monomer composition. Thus, powder or hydrophobic silica instead of colloidal silica does not have rewet improvement effect, and thus, cannot achieve the effect intended in the present invention.

As the colloidal silica fulfilling such a requirement, ST-O, ST-AK, and the like (Nissan Chemical Corporation) may be mentioned, but the present invention is not limited thereto.

In the preparation method of the present invention, the monomer composition may further comprise a foaming agent, and/or a foam stabilizer.

The foaming agent performs a function for foaming during polymerization to form pores in hydrogel polymer, thus increasing the surface area. As the foaming agent, a capsule type foaming agent and/or carbonate may be used, and as the carbonate foaming agent, for example, sodium bicarbonate, sodium carbonate, potassium bicarbonate, potassium carbonate, calcium bicarbonate, calcium bicarbonate, magnesium bicarbonate or magnesium carbonate may be used, but the present invention is not limited thereto.

And, the foaming agent may be added in the concentration of about 0.005 to about 1 part by weight, or about 0.01 to about 0.3 parts by weight, based on 100 parts by weight of the acrylic acid-based monomers. If the amount of the foaming agent used is greater than 1 part by weight, there may be too many pores, and thus, gel strength and density of super absorbent polymer may decrease, thus causing problems in terms of distribution and storage. And, if it is less than 0.005 parts by weight, function as a foaming agent may be insignificant.

And, the foam stabilizer performs functions for maintaining the shape of the foams formed by the foaming agent, and simultaneously, uniformly distributing the foams over the whole area of polymer, thereby increasing the surface area of polymer.

As the foam stabilizer, anionic surfactant may be used, and as the examples of anionic surfactant that can be used, sodium dodecyl sulfate, sodium stearate, ammonium lauryl sulfate, sodium lauryl ether sulfate, sodium myreth sulfate, or alkylether sulfate-based compounds similar to the above compounds may be mentioned. The anionic surfactant that can be used is not limited thereto, but preferably, sodium dodecyl sulfate or sodium stearate may be used.

The anionic surfactant may be added in the concentration of about 0.001 to about 1 part by weight, or about 0.005 to about 0.05 parts by weight, based on 100 parts by weight of the acrylic acid-based monomers. If the concentration of the anionic surfactant is too low, function as a foam stabilizer may be insignificant, and thus, it may be difficult to achieve the effect of improving absorption speed, and if the concentration is too high, centrifuge retention capacity and absorption speed may be lowered to the contrary, which is not preferable.

In the preparation method, the monomer composition may further comprise additives such as a thickener, a plasticizer, a preservation stabilizer, an antioxidant, etc., as necessary.

The above explained raw materials such as acrylic acid-based monomers having acid groups, of which at least part are neutralized, a photopolymerization initiator, a thermal polymerization initiator, an internal crosslinking agent, and additives may be prepared in the form of a solution dissolved in a solvent.

Here, the solvent that can be used is not limited in terms of its construction as long as it can dissolve or disperse the above explained raw materials, and for example, one or more selected from water, ethanol, ethyleneglycol, diethyleneglycol, triethyleneglycol, 1,4-butanediol, propyleneglycol, ethyleneglycol monobutyl ether, propyleneglycol monomethyl ether, propyleneglycol monomethyl ether acetate, methylethylketone, acetone, methylamylketone, cyclohexanone, cyclopentanone, diethyleneglycol monomethyl ether, diethyleneglycol ethyl ether, toluene, xylene, butyrolactone, carbitol, methylcellosolve acetate and N,N-dimethylacetamide, etc. may be used alone or in combination.

The solvent may be included in the remaining amount except the above described components, based on the total content of the monomer composition.

Meanwhile, a method of forming hydrogel polymer by thermal polymerization or photopolymerization of the monomer composition is not specifically limited in terms of its construction, as long as it is a commonly used polymerization method.

Specifically, the polymerization method is largely classified into thermal polymerization and photopolymerization according to an energy source. Commonly, thermal polymerization may be progressed in a reactor equipped with a stirring axis such as a kneader, and, photopolymerization may be progressed in a reactor equipped with a movable conveyer belt or a container having a flat bottom, but the above explained polymerization methods are no more than examples, and the present invention is not limited thereto.

For example, hydrogel polymer may be obtained by introducing the above described monomer composition into a reactor equipped with a stirring axis such as a kneader, and supplying hot air or heating the reactor to progress thermal polymerization. Here, the hydrogel polymer discharged to the outlet of the reactor may in the size of a few centimeters to a few millimeters according to the shape of the stirring axis equipped in the reactor. Specifically, the size of obtained hydrogel polymer may vary according to the concentration of the introduced monomer composition and the introduction speed, etc., and commonly, hydrogel polymer with a (weight average) particle diameter of 2 to 50 mm may be obtained.

And, in case photopolymerization of the monomer composition is progressed in a reactor equipped with a movable conveyer belt or a container having a flat bottom as explained above, hydrogel polymer in the form of a sheet having a width of the belt may be obtained. Here, the thickness of the sheet may vary according to the concentration of the introduced monomer composition and the introduction speed or introduction amount, but it is preferable that the monomer composition is fed so as to obtain polymer in the form of sheet having a thickness of about 0.5 to about 5 cm. If a monomer composition is fed so that the thickness of sheet polymer may become too thin, production efficiency may be low, and if the thickness of sheet polymer is greater than 5 cm, due to the excessively thick thickness, polymerization may not uniformly occur over the whole thickness.

Here, the moisture content of hydrogel polymer obtained by such a method may be about 40 to about 80 wt %. Throughout the specification, the "moisture content" is the content of moisture occupied based on the total weight of hydrogel polymer, and it means a value obtained by subtracting the weight of polymer of a dry state from the weight of hydrogel polymer. Specifically, it is defined as a value calculated by measuring the weight loss according to moisture evaporation in the polymer while raising the temperature of polymer through infrared heating to dry. At this time, the drying condition is set up such that the temperature is raised from room temperature to about 180° C. and then maintained at 180° C., and the total drying time is 40 minutes including a temperature raising step of 5 minutes.

Next, the obtained hydrogel polymer is dried.

Wherein, a coarse grinding step may be further conducted before drying the hydrogel polymer so as to increase drying efficiency.

Here, grinders that can be used in the coarse grinding is not limited in terms of the constructions, but specifically, one selected from the group consisting of a vertical pulverizer, a turbo cutter, a turbo grinder, a rotary cutter mill, a cutter mill, a disc mill, a shred crusher, a crusher, a chopper, a disc cutter may be used, but the grinder is not limited thereto.

Through the coarse grinding step, the particle diameter of the hydrogel polymer may be controlled to about 2 to about 10 mm.

Grinding to a particle diameter less than 2 mm would not be technically easy due to the high moisture content of hydrogel polymer, and cause caking between ground particles. Meanwhile, if grinding to a particle diameter greater than 10 mm, the effect for increasing the efficiency in the subsequent drying step may be insignificant.

The hydrogel polymer coarsely ground as explained above, or hydrogel polymer immediately after polymerization that is not subjected to the coarse grinding step is dried. Here, the drying temperature may be about 150 to about 250° C. If the drying temperature is less than 150° C., a drying time may become excessively long, and the properties of the finally formed super absorbent polymer may be deteriorated, and if the drying temperature is greater than 250° C., only the surface of polymer may be dried to generate fine powders in the subsequent grinding process, and the properties of the finally formed super absorbent polymer may be deteriorated. Thus, it is preferable that the drying is progressed at a temperature of about 150 to about 200° C., more preferably about 160 to about 180° C.

Meanwhile, a drying time may be about 20 to about 90 minutes, considering process efficiency, and the like, but is not limited thereto.

And, the drying method is not limited in terms of the construction as long as it is commonly used as a drying process of hydrogel polymer. Specifically, the drying step may be progressed by hot wind supply, infrared ray irradiation, ultrahigh frequency wave irradiation, or UV irradiation, etc. The polymer dried by such a method may exhibit a moisture content of about 0.1 to about 10 wt %.

Next, the dried polymer obtained through the drying step is ground.

The particle diameter of the polymer powder obtained after the grinding step may be 150 μm to 850 μm. As a grinder for grinding to such a particle diameter, specifically, a pin mill, a hammer mill, a screw mill, a roll mill, a disc mill, or a jog mill, etc. may be used, but the grinder is not limited thereto.

And, in order to manage the properties of the super absorbent polymer powders finally productized after the grinding step, the polymer powders obtained after grinding may be subjected to a separate process of sieving according to the particle diameter.

Next, hydrophobic material having a melting temperature (Tm) of 40 to 80° C., and water solubility at 25° C. of 70 mg/L or less, and an epoxy-based surface crosslinking agent are mixed with the base resin (Step 2).

In a common preparation method of super absorbent polymer, dried and ground polymer, namely, base resin is mixed with a surface crosslinking solution comprising a surface crosslinking agent, and then, the mixture is heated to raise temperature, thereby conducting a surface crosslinking reaction of the ground polymer.

The surface crosslinking step is a step of inducing a crosslinking reaction on the surface of ground polymer in the presence of a surface crosslinking agent, thereby forming super absorbent polymer having more improved properties. Through the surface crosslinking, a surface crosslink layer (surface modification layer) is formed on the surface of ground polymer particles.

In general, since a surface crosslinking agent is coated on the surface of super absorbent polymer particles, a surface crosslinking reaction occurs on the surface of super absorbent polymer particles, and it improves crosslinkability on the surface of the particles without substantially influencing the inside of the particles. Thus, surface crosslinked super absorbent polymer particles have higher crosslinking degree around the surface than inside.

Meanwhile, as the surface cross-linking agent, compounds capable of reacting with the functional groups of polymer may be used, and for example, polyhydric alcohol compounds, epoxy compounds, polyamine compounds, haloepoxy compounds, condensation products of haloepoxy compounds, oxazoline compounds, multivalent metal salts, or alkylene carbonate compounds, and the like may be used.

Meanwhile, according to the preparation method of the present invention, an epoxy-based surface cross-linking agent, particularly an epoxy-based surface cross-linking agent capable of progressing a surface cross-linking reaction with base resin at 110 to 170° C. may be used to improve rewet property. The present inventors confirmed that in case other surface cross-linking agents that progress a surface cross-linking reaction at high temperature greater than 170° C., such as diol-based, alkylene carbonate-based compounds, etc. are used, rewet property may be deteriorated by surface cross-linking to the contrary.

Examples of the epoxy-based surface cross-linking agent fulfilling the above requirement, ethyleneglycol diglycidyl ether, diethyleneglycol diglycidyl ether, triethyleneglycol diglycidyl ether, tetraethyleneglycol diglycidyl ether, glycerin polyglycidyl ether, or sorbitol polyglycidyl ether, and the like may be mentioned.

The content of the epoxy-based surface cross-linking agent added may be about 0.005 parts by weight or more, or about 0.01 parts by weight or more, or about 0.02 parts by weight or more, and about 0.5 parts by weight or less, about 0.2 parts by weight or less, or about 0.1 parts by weight or less, or 0.05 parts by weight or less, based on 100 parts by weight of the base resin.

If the content of the epoxy-based surface cross-linking agent is too small, the cross-linking density of the surface crosslink layer may be too low, and thus, absorption properties such as absorption under pressure and permeability may be deteriorated, and if it is excessively used, due to excessive progression of surface cross-linking reaction, rewet property may be deteriorated.

The epoxy-based surface cross-linking agent may be added in the form of a surface cross-linking solution by additionally mixing water when adding the epoxy-based surface cross-linking agent. If water is added, the surface cross-linking agent may be uniformly dispersed in polymer. Wherein, it is preferable that water is added in the content of about 1 to about 10 parts by weight, based on 100 parts by weight of the polymer, so as to induce uniform dispersion of the surface cross-linking agent, preventing caking of polymer powder, and optimizing the surface penetration depth of the surface cross-linking agent.

Meanwhile, although absorption properties may be increased by the surface cross-linking reaction, rewet property may be lowered.

However, according to the present invention, by mixing hydrophobic material with base resin before mixing the epoxy-based surface cross-linking agent with base resin and raising temperature to progress a surface cross-linking reaction, improvement in rewet property and vortex time may be simultaneously achieved.

As the hydrophobic material, materials fulfilling a melting temperature (Tm) 40° C. of more, or 45° C. or more, or 50° C. or more, and 80° C. or less, or 75° C. or less, or 70° C. or less may be used. If the melting temperature of the hydrophobic material is too low, flowability of the product may be deteriorated, and if material having excessively high melting temperature is used, hydrophobic material cannot be uniformly coated on the surface of particle during the surface cross-linking process, and thus, hydrophobic material having the above melting temperature range is used.

And, as the hydrophobic material, materials substantially insoluble in water, or having solubility of 70 mg/L or less, or 65 mg/L or less, or 50 mg/L or less at 25° C. may be used.

As the hydrophobic material fulfilling the requirements, for example, lauric acid, myristic acid, cetyl alcohol, stearic acid, glycol stearate, glycerol monostearate, glycol distearate, stearin, pentaerythrityl distearate, oleamide, and the like may be mentioned, but the present invention is not limited thereto.

The melting temperatures and water solubilities of some illustrative hydrophobic materials are shown in the following Table 1.

TABLE 1

| Material | Tm (° C.) | Water solubility (at 25° C.) |
| --- | --- | --- |
| Lauric Acid | 43 | 63 mg/L |
| Myristic acid | 54.4 | 24 mg/L |
| Cetyl Alcohol | 49 | insoluble |
| Stearic Acid | 69.3 | 3.4 mg/L |
| Glycol Stearate | 55~60 | insoluble |
| Glycerol Monostearate | 58~59 | insoluble |
| Glycol Distearate | 65~73 | Insoluble |
| Stearin | 54~72.5 | insoluble |
| Pentaerythrityl Distearate | 48~52 | insoluble |
| PEG150 Distearate | 52~57 | insoluble |
| PEG Stearyl Alcohol | 57 | insoluble |
| Glyceryl Laurate | 56~60 | insoluble |
| Oleamide | 70 | insoluble |

The hydrophobic material is distributed in the surface modification layer of the base resin, and it may prevent the aggregation or caking of swollen polymer particles by increased pressure, while the super absorbent polymer absorbs liquid and is swollen, and may afford hydrophobicity to the surface, thereby facilitating the penetration and diffusion of liquid. Thus, it may contribute to improvement in the rewet property of super absorbent polymer.

The hydrophobic material may be mixed in the content of about 0.02 parts by weight or more, or about 0.025 parts by weight or more and about 0.5 parts by weight or less, or about 0.3 parts by weight or less, or about 0.1 parts by weight or less, based on 100 parts by weight of the base resin. If the content of the hydrophobic material is too small, it may not be sufficient for improving rewet property, and if the hydrophobic material is excessively included, wettability may be deteriorated, or base resin and hydrophobic material may be separated from each other, thus acting as impurities, and thus, the above range is preferable.

A method of mixing the hydrophobic material is not specifically limited as long as it can uniformly mix it with the base resin.

For example, the hydrophobic material may be dry mixed before a surface crosslinking solution comprising an epoxy-based surface crosslinking agent is mixed with the base resin, or it may be dispersed in the surface crosslinking solution together with a surface crosslinking agent and mixed with the base resin. Alternatively, separately from the surface crosslinking solution, the hydrophobic material may be heated above the melting point and mixed in a solution state.

The existence and content of the hydrophobic material in super absorbent polymer may be measured by preparing a standard solution and using HPLC (high-performance liquid chromatography) and/or CAD (charged aerosol detector), and the content of the hydrophobic material measured by HLPC and/or CAD may be about 40 to 90 wt % of total hydrophobic material introduced.

Meanwhile, in addition to the above explained surface crosslinking agent, multivalent metal salts, for example, one or more selected from the group consisting of aluminum salts, more specifically, sulfates, potassium salts, ammonium salts, sodium salts and hydrochloride of aluminum may be further included.

By additionally using such a multivalent metal salt, permeability of the super absorbent polymer prepared by the method of one embodiment can be further improved. Such a multivalent metal salt may be added to the surface crosslinking solution together with the surface crosslinking agent, and it may be used in the content of about 0.01 to 4 parts by weight, based on 100 parts by weight of the base resin.

Next, the mixture of base resin, hydrophobic material, and an epoxy-based surface cross-linking agent is heated to increase the temperature, thereby conducting a surface modification step of the base resin (step 3).

The surface modification step may be conducted by heating at a temperature of about 100 to about 170° C., preferably about 110 to about 160° C. for about 10 to about 90 minutes, preferably about 20 to about 70 minutes. If the crosslinking reaction temperature is less than 100° C. or the reaction time is too short, a surface crosslinking reaction may not properly occur, and thus, permeability may decrease, and if the temperature is greater than 170° C. or the reaction time is too long, centrifuge retention capacity may be deteriorated.

A temperature rise means for the surface modification reaction is not specifically limited. A heating medium may be supplied, or a heat source may be directly supplied to heat. Here, the kinds of the heating medium that can be used may include temperature-increased fluid such as steam, hot air, hot oil, etc., but are not limited thereto, and the temperature of the heating medium supplied may be appropriately selected considering the means of the heating medium, temperature rise speed and a temperature to be increased. Meanwhile, the heat source directly supplied may include electric heating, gas heating, etc., but is not limited thereto.

By the surface modification step, on the surface of the base resin, a surface crosslink structure that is formed by the reaction of the epoxy-based surface crosslinking agent and the functional groups of the base resin may be formed, and a surface modification layer in which the above explained hydrophobic material is uniformly distributed in the surface crosslink structure may be formed.

In the preparation method of the present invention, inorganic filler may be additionally mixed with the base resin in the step 2, or inorganic filer may be mixed with the super absorbent polymer passing through the step 3.

Specifically, before raising temperature to conduct a surface modification reaction, inorganic filler may be additionally mixed with the base resin, or inorganic filler may be mixed with super absorbent polymer by dry mixing the inorganic filler with the super absorbent polymer on which a surface modification layer is formed by conducting the surface modification reaction of step 3.

According to the present invention, by additionally mixing inorganic filler, anti-caking effect may be provided.

As the inorganic filler, hydrophobic or hydrophilic filler may be mixed, and for example, silica particles such as fumed silica, precipitated silica, and the like may be used, but the present invention is not limited thereto.

And, the inorganic filler may be added in the concentration of about 0.01 to about 0.5 parts by weight, or about 0.02 to about 0.2 parts by weight, based on 100 parts by weight of the base resin or super absorbent polymer. If the amount of the inorganic filler used is greater than 0.5 parts by weight, absorption property such as absorption under pressure may be deteriorated, and if it is less than 0.01 parts by weight, anti-cake effect may not be exhibited, and thus, it is preferable that the inorganic filler is used in the above range.

As explained above, according to the preparation method of the present invention, since acrylic acid-based monomers are polymerized to prepare base resin, and hydrophobic material and an epoxy-based surface cross-linking agent are added to the base resin, thus progressing a surface modification reaction to form a surface modification layer, rewet improvement effect may be exhibited, and since inorganic filler is mixed with the super absorbent polymer on which the surface modification layer is formed or with the base resin, anti-cake effect may be exhibited.

Thus, according to the preparation method of the present invention, due to the properties of the base resin, and the combined actions of the surface modification layer formed on the base resin and inorganic filler, super absorbent polymer having improved rewet property and rapid vortex time, in which caking is prevented, can be provided without deteriorating the properties such as centrifuge retention capacity, and absorption under pressure, and the like.

For example, the super absorbent polymer may have centrifuge retention capacity (CRC) measured according to EDANA method WSP 241.3, in the range of about 20 g/g or more, or 30 g/g or more, or about 31 g/g or more, and about 40 g/g or less, or about 38 g/g or less, or about 35 g/g or less.

And, the super absorbent polymer may have absorption under pressure (AUP) of 0.3 psi, measured according to EDANA method WSP 242.3, in the range of about 26 g/g or more, or about 27 g/g or more, or about 28 g/g or more, and about 35 g/g or less, or about 33 g/g or less, or about 32 g/g or less.

And, the super absorbent polymer of the present invention may have extractable contents (EC) measured according to EDANA method WSP 270.2, of about 9.0 wt % or less, or 7.5 wt % or less, or 7.0 wt % or less. The extractable contents (EC) is more excellent as it is smaller, and thus, the lower limit of the water extractable contents (EC) is theoretically 0 wt %, but for example, it may be about 1.0 wt % or more, or about 2.0 wt % or more, or about 3.0 wt % or more.

And, the super absorbent polymer may have a vortex time of 35 seconds or less, or 32 seconds or less, or about 31 seconds or less. The vortex time is more excellent as it is smaller, and thus, the lower limit of the vortex time is theoretically 0 second, but for example, it may be about 5 seconds or more, or about 10 seconds or more, or about 12 seconds or more.

The vortex time means a time (unit: second) taken until liquid vortex disappears by rapid absorption, when super absorbent polymer is added to a saline solution and stirred, and it is considered that as the time is shorter, super absorbent polymer has more rapid initial absorption speed.

And, the super absorbent polymer may have permeability measured according to the following Equation 1, of 40 seconds or less, or 30 seconds or less, or 25 seconds or less. The permeability is more excellent as the value is smaller, and thus, the lower limit is theoretically 0 second, but for example, it may be about 5 seconds or more, or about 10 seconds or more, or about 12 seconds or more.

Permeability (sec)=$T1-B$ in the Equation 1, $T1$ is a time taken until the height of a liquid level decreases from 40 ml to 20 ml, after putting 0.2±0.0005 g of a sieved (30#~50#) super absorbent polymer sample in a chromatography column and adding brine to the volume of 50 ml, and then, leaving it for 30 minutes; and B is a time taken until the height of a liquid level decreases from 40 ml to 20 ml in a chromatography column filled with brine.

And, the super absorbent polymer may not only exhibit excellent absorption properties, but also exhibit more improved rewet property.

More specifically, the rewet property (tap water short-term rewet under no pressure) may be 1.5 g or less, or 1.2 g or less, or 1.0 g or less, or 0.9 g or less, or 0.8 g or less, or 0.7 g or less, said rewet property being defined by the weight of water exuding from super absorbent polymer to a filter paper, after 1 g of the super absorbent polymer is soaked in 100 g of tap water to swell for 10 minutes, and then, the swollen super absorbent polymer is left on the filter paper for 1 hour from the first time when it is soaked in the tap water. As the weight of water is smaller, the rewet property is more excellent, and thus, the lower limit is theoretically 0 g, but for example, it may be 0.1 g or more, or 0.2 g or more, or 0.3 g or more.

And, the super absorbent polymer may have rewet property (tap water long-term rewet under pressure) of 1.5 g or less, or 1.2 g or less, or 1.0 g or less, or 0.9 g or less, or 0.8 g or less, or 0.7 g or less, said rewet property being defined by the weight of water exuding from super absorbent polymer to a filter paper, after 4 g of the super absorbent polymer is soaked in 200 g of tap water to swell for 2 hours, and then, the swollen super absorbent polymer is left on the filter paper for 1 minute under pressure of 0.75 psi.

In the rewet property evaluation, the tap water used may have electric conductivity of 170 to 180 μS/cm. Since the electric conductivity of tap water significantly influences the properties measured, there is a need to measure the properties such as rewet property using tap water having electric conductivity of an equivalent level.

As explained above, the super absorbent polymer of the present invention has excellent absorption power and absorption speed, and even if it absorbs a large quantity of urine, rewet and urine leakage may be inhibited. Thus, the super absorbent polymer of the present invention may be suitably used as fillers of thin or ultrathin hygienic products.

The present invention will be explained in more detail in the following examples. However, these examples are presented only as the illustrations of the present invention, and the scope of the present invention is not limited thereby.

EXAMPLE

Preparation of Super Absorbent Polymer

Example 1

In a 3 L glass container equipped with a stirrer and a thermometer, 600 g of acrylic acid, 0.003 g of PEGDA400

(polyethyleneglycol diacrylate 400) and 1.5 g of EX810 (ethyleneglycol diglycidyl ether, ethyleneglycol diglycidyl ether) as internal cross-linking agents, 0.048 g of diphenyl (2,4,6-trimethylbenzoyl)-phosphine oxide as a photoinitiator, 0.6 g of sodium persulfate (SPS) as a thermal initiator, 0.03 g of sodium dodecyl sulfate as surfactant, and 974.7 g of 24.0% sodium hydroxide solution were mixed to prepare an aqueous solution of water soluble unsaturated monomers (neutralization degree: 70 mol %, solid content: 45 wt %).

Thereafter, when the temperature of the aqueous monomer solution became 50° C., 0.48 g of a capsule type foaming agent 140DS was added and mixed, and then, UV was irradiated for 1 minute (the amount of irradiation: 10 mW/cm$^2$) to conduct UV polymerization and obtain hydrogel polymer. The obtained hydrogel polymer was ground to 2 mm*2 mm, and then, the moisture content (180° C., 40 minutes) was measured to be 47%.

The obtained gel type resin was spread on a stainless wire gauze having a pore size of 600 μm to a thickness of about 30 mm, and dried in a 180° C. hot air oven for 30 minutes. The obtained dried polymer was ground with a grinder, and sieved with a standard sieve of ASTM standard, thus obtaining base resin having particles size of 150 to 850 μm.

Thereafter, a surface treatment solution comprising 0.03 parts by weight of EX810 (ethyleneglycol diglycidyl ether), 6 parts by weight of water, 0.1 parts by weight of Al—S, 0.1 parts by weight of inorganic filler (Aerosil 200), 0.025 parts by weight of glycerol monostearate, and 0.025 parts by weight of polyethyleneglycol (PEG, Mw: 6,000 g/mol) was uniformly mixed with 100 parts by weight of the prepared base resin, and then, the mixture was fed to one surface cross-linking reactor, and a surface cross-linking reaction of the base resin was progressed at 140° C. for 40 minutes. After completing the surface treatment, surface treated super absorbent polymer having average particle size of 150 to 850 μm was obtained using a sieve.

Example 2

Super absorbent polymer was prepared by the same method as Example 1, except that 0.025 parts by weight of lauric acid was used instead of 0.025 parts by weight of glycerol monostearate in the surface treatment solution of Example 1.

Example 3

Super absorbent polymer was prepared by the same method as Example 1, except that 0.025 parts by weight of myristic acid was used instead of 0.025 parts by weight of glycerol monostearate in the surface treatment solution of Example 1.

Example 4

Super absorbent polymer was prepared by the same method as Example 1, except that 0.025 parts by weight of cetyl alcohol was used instead of 0.025 parts by weight of glycerol monostearate in the surface treatment solution of Example 1.

Example 5

Super absorbent polymer was prepared by the same method as Example 1, except that 0.025 parts by weight of stearic acid was used instead of 0.025 parts by weight of glycerol monostearate in the surface treatment solution of Example 1.

Example 6

Super absorbent polymer was prepared by the same method as Example 1, except that 0.025 parts by weight of glycol distearate was used instead of 0.025 parts by weight of glycerol monostearate in the surface treatment solution of Example 1.

Example 7

Super absorbent polymer was prepared by the same method as Example 1, except that 0.025 parts by weight of stearin was used instead of 0.025 parts by weight of glycerol monostearate in the surface treatment solution of Example 1.

Example 8

Super absorbent polymer was prepared by the same method as Example 1, except that 0.025 parts by weight of pentaerythrityl distearate was used instead of 0.025 parts by weight of glycerol monostearate in the surface treatment solution of Example 1.

Example 9

Super absorbent polymer was prepared by the same method as Example 1, except that 0.025 parts by weight of PEG150 distearate was used instead of 0.025 parts by weight of glycerol monostearate in the surface treatment solution of Example 1.

Example 10

Super absorbent polymer was prepared by the same method as Example 1, except that 0.025 parts by weight of PEG stearyl alcohol was used instead of 0.025 parts by weight of glycerol monostearate in the surface treatment solution of Example 1.

Example 11

Super absorbent polymer was prepared by the same method as Example 1, except that 0.025 parts by weight of glyceryl laurate was used instead of 0.025 parts by weight of glycerol monostearate in the surface treatment solution of Example 1.

Example 12

Super absorbent polymer was prepared by the same method as Example 1, except that 0.025 parts by weight of oleamide was used instead of 0.025 parts by weight of glycerol monostearate in the surface treatment solution of Example 1.

Example 13

Super absorbent polymer was prepared by the same method as Example 1, except that 12 g of ST-O (Snowtex O, Nissan Chemical, solid contents 20 wt %) was additionally mixed with the aqueous monomer solution as colloidal silica, and EX810 was used in the content of 0.1 parts by weight in the surface treatment solution.

Example 14

Super absorbent polymer was prepared by the same method as Example 1, except that glycerol monostearate was used in the content of 0.02 parts by weight in the surface treatment solution of Example 1.

Example 15

Super absorbent polymer was prepared by the same method as Example 1, except that glycerol monostearate was used in the content of 0.050 parts by weight in the surface treatment solution of Example 1.

Example 16

Super absorbent polymer was prepared by the same method as Example 1, except that 2.0 g of ST-AK (Nissan, solid contents 30 wt %) was additionally mixed with the aqueous monomer solution as colloidal silica.

Example 17

Super absorbent polymer was prepared by the same method as Example 1, except that 8.0 g of ST-AK (Nissan, solid contents 30 wt %) was additionally mixed with the aqueous monomer solution as colloidal silica.

Example 18

Base resin was prepared by the same method as Example 1.

Thereafter, 0.025 parts by weight of glycerol monostearate was dry mixed with 100 parts by weight of the prepared base resin, and then, a surface treatment solution comprising 0.03 parts by weight of EX810 (ethyleneglycol diglycidyl ether), 6 parts by weight of water, 0.1 parts by weight of Al—S, 0.1 parts by weight of inorganic filler (Aerosil 200), 0.025 parts by weight of polyethyleneglycol (PEG, Mw: 6,000 g/mol) was uniformed mixed therewith, the mixture was fed to one surface cross-linking reactor, and a surface cross-linking reaction of the base resin was progressed at 140° C. for 40 minutes.

After the surface treatment was completed, surface treated super absorbent polymer having average particle diameter of 150 to 850 μm was obtained using a sieve.

Example 19

Super absorbent polymer was prepared by the same method as Example 1, except that PEGDA400 was used in the amount of 0.012 g in the aqueous monomer solution of Example 1.

Example 20

Super absorbent polymer was prepared by the same method as Example 1, except that PEGDA400 was used in the amount of 0.0015 g in the aqueous monomer solution of Example 1.

Example 21

Super absorbent polymer was prepared by the same method as Example 1, except that PEGDA400 was used in the amount of 0.03 g in the aqueous monomer solution of Example 1.

Example 22

Super absorbent polymer was prepared by the same method as Example 1, except that PEGDA400 was used in the amount of 0.002 g in the aqueous monomer solution of Example 1.

Comparative Example 1

In a 3 L glass container equipped with a stirrer and a thermometer, 600 g of acrylic acid, 2.22 g of PEGDA400 (polyethyleneglycol diacrylate 400) as an internal cross-linking agents, 0.048 g of diphenyl(2,4,6-trimethylbenzoyl)-phosphine oxide as a photoinitiator, 0.6 g of sodium persulfate (SPS) as a thermal initiator, 0.03 g of sodium dodecyl sulfate as surfactant, and 974.7 g of 24.0% sodium hydroxide solution were mixed to prepare an aqueous solution of water soluble unsaturated monomers (neutralization degree: 70 mol %, solid content: 45 wt %).

Thereafter, when the temperature of the monomer solution became 50° C., 0.48 g of a capsule type foaming agent 140DS was added and mixed, and then, UV was irradiated for 1 minute (the amount of irradiation: 10 mW/cm$^2$) to conduct UV polymerization and obtain hydrogel polymer. The obtained hydrogel polymer was ground to 2 mm*2 mm, and then, the moisture content was measured to be 47%.

The obtained gel type resin was spread on a stainless wire gauze having a pore size of 600 μm to a thickness of about 30 mm, and dried in a 180° C. hot air oven for 30 minutes. The obtained dried polymer was ground with a grinder, and sieved with a standard sieve of ASTM standard, thus obtaining base resin having particles size of 150 to 850 μm.

Thereafter, a surface treatment solution comprising 0.03 parts by weight of EX810 (ethyleneglycol diglycidyl ether), 6 parts by weight of water, 0.1 parts by weight of Al—S, 0.1 parts by weight of inorganic filler (Aerosil 200), 0.025 parts by weight of polyethyleneglycol (PEG, Mw: 6,000 g/mol) was uniformly mixed with 100 parts by weight of the prepared base resin, and then, the mixture was fed to one surface cross-linking reactor, and a surface cross-linking reaction of the base resin was progressed at 140° C. for 40 minutes.

After completing the surface treatment, surface treated super absorbent polymer having average particle size of 150 to 850 μm was obtained using a sieve.

Comparative Example 2

Base resin was prepared by the same method as Comparative Example 1.

Thereafter, a surface treatment solution comprising 0.1 parts by weight of 1,3-propanediol, 6 parts by weight of water, 0.1 parts by weight of Al—S, 0.1 parts by weight of inorganic filler (Aerosil 200), 0.025 parts by weight of glycerol monostearate, and 0.025 parts by weight of polyethyleneglycol (PEG, Mw: 6,000 g/mol) was mixed with 100 parts by weight of the prepared base resin, and a surface cross-linking reaction of the base resin was progressed at 140° C. for 40 minutes, thus preparing super absorbent polymer.

Comparative Example 3

Base resin was prepared by the same method as Comparative Example 1.

Thereafter, a surface treatment solution comprising 0.1 parts by weight of ethylene carbonate, 6 parts by weight of water, 0.1 parts by weight of Al—S, 0.1 parts by weight of inorganic filler (Aerosil 200), 0.025 parts by weight of glycerol monostearate, and 0.025 parts by weight of polyethyleneglycol (PEG, Mw: 6,000 g/mol) was mixed with 100 parts by weight of the prepared base resin, and a surface cross-linking reaction of the base resin was progressed at 140° C. for 40 minutes, thus preparing super absorbent polymer.

Comparative Example 4

In a 3 L glass container equipped with a stirrer and a thermometer, 600 g of acrylic acid, 0.6 g of PEGDA400 (polyethyleneglycol diacrylate 400) and 0.6 g of EX810 (ethyleneglycol diglycidyl ether) as internal cross-linking agents, 0.048 g of diphenyl(2,4,6-trimethylbenzoyl)-phosphine oxide as a photoinitiator, 0.6 g of sodium persulfate (SPS) as a thermal initiator, 0.03 g of sodium dodecyl sulfate as surfactant, and 974.7 g of 24.0% sodium hydroxide solution were mixed to prepare an aqueous solution of water soluble unsaturated monomers (neutralization degree: 70 mol %, solid content: 45 wt %).

Thereafter, when the temperature of the monomer solution became 50° C., 0.48 g of a capsule type foaming agent 140DS was added and mixed, and then, UV was irradiated for 1 minute (the amount of irradiation: 10 mW/cm$^2$) to conduct UV polymerization and obtain hydrogel polymer. The obtained hydrogel polymer was ground to 2 mm*2 mm, and then, the moisture content was measured to be 47%.

The obtained gel type resin was spread on a stainless wire gauze having a pore size of 600 μm to a thickness of about 30 mm, and dried in a 180° C. hot air oven for 30 minutes. The obtained dried polymer was ground with a grinder, and sieved with a standard sieve of ASTM standard, thus obtaining base resin having particles size of 150 to 850 μm.

Thereafter, a surface treatment solution comprising 0.03 parts by weight of EJ1030 (ethyleneglycol diglycidyl ether), 6 parts by weight of water, 0.1 parts by weight of Al—S, 0.1 parts by weight of inorganic filler (Aerosil 200), 0.025 parts by weight of glycerol monostearate, and 0.025 parts by weight of polyethyleneglycol (PEG, Mw: 6,000 g/mol) was uniformly mixed with 100 parts by weight of the prepared base resin, and then, the mixture was fed to one surface cross-linking reactor, and a surface cross-linking reaction of the base resin was progressed at 140° C. for 40 minutes.

After completing the surface treatment, surface treated super absorbent polymer having average particle size of 150 to 850 μm was obtained using a sieve.

Comparative Example 5

Super absorbent polymer was prepared by the same method as Example 1, except that PEGDA400 was used in the amount of 0.001 g in the aqueous monomer solution of Example 1.

Comparative Example 6

Super absorbent polymer was prepared by the same method as Example 1, except that PEGDA400 was used in the amount of 0.048 g in the aqueous monomer solution of Example 1.

Comparative Example 7

Super absorbent polymer was prepared by the same method as Example 1, except that PEGDA400 was used in the amount of 0.06 g in the aqueous monomer solution of Example 1.

EXPERIMENTAL EXAMPLE

For the super absorbent polymer prepared in Examples and Comparative Examples, the properties were evaluated as follows.

Unless otherwise indicated, all the property evaluations were progressed at constant temperature constant humidity (23±1° C., relative humidity 50±10%), and a saline solution or brine means an aqueous solution of 0.9 wt % sodium chloride (NaCl).

And, in the following rewet property evaluation, as the tap water, tap water having electric conductivity of 170 to 180 μS/cm, when measured using Orion Star A222 (Thermo Scientific), was used.

(1) Centrifuge Retention Capacity (CRC)

Centrifuge retention capacity by absorption rate under no load was measured according to EDANA WSP 241.3.

Specifically, $W_0(g)$ (about 0.2 g) of super absorbent polymer was uniformly put in an envelope made of nonwoven fabric and sealed, and then, soaked in a saline solution (0.9 wt %) at room temperature. After 30 minutes, it was drained for 3 minutes under 250 G using a centrifuge, and the weight $W_2(g)$ of the envelope was measured. And, the same operation was conducted without using polymer, and then, the weight $W_1(g)$ at that time was measured. Using each obtained weight, CRC (g/g) was calculated according to the following Mathematical Formula.

$$CRC\ (g/g)=\{[W_2(g)-W_1(g)]/W_0(g)\}-1 \quad \text{[Mathematical Formula 1]}$$

(2) Absorption Under Pressure (AUP)

For each polymer, absorption under pressure of 0.3 psi was measured according to EDANA method WSP 242.3.

Specifically, on the bottom of a plastic cylinder having an inner diameter of 60 mm, a 400 mesh wire netting made of stainless was installed. Under room temperature and 50% humidity conditions, $W_0(g)$ (0.9 g) of super absorbent polymer was uniformly sprayed on the wire netting, and a piston having an outer diameter slightly smaller than 60 mm and capable of further giving 0.3 psi load was installed thereon so that there was no gap with the inner wall of the cylinder and the up and down movement was not hindered. At this time, the weight $W_3(g)$ of the device was measured.

Inside a petri dish having a diameter of 150 mm, a glass filter having a diameter of 90 mm and a thickness of 5 mm was laid, and a saline solution consisting of 0.9 wt % sodium chloride was put to the same level with the upper side of the glass filter. One piece of a filter paper was laid thereon. On the filter paper, the measuring device was laid, and the liquid was absorbed under pressure for 1 hour. After 1 hour, the measuring device was lifted, and the weight $W_4(g)$ was measured.

Using each obtained weight, absorption under pressure (g/g) was calculated according to the following Mathematical Formula.

$$AUP(g/g)=[W_4(g)-W_3(g)]/W_0(g) \quad \text{[Mathematical Formula 2]}$$

(3) Permeability

While a piston was put in the chromatography column (F20 mm), lines were marked at the liquid levels corresponding to the liquid amounts 20 ml and 40 ml. Thereafter, between the glass filter on the bottom of the chromatography column and a cock, water was inversely introduced so as not to generate bubbles, and filled up to about 10 ml, followed by washing with brine twice to three times, and filling with 0.9% brine up to 40 ml or more. A piston was put in the chromatography column, the lower valve was opened, and a time (B) taken until the liquid level decreased from the marked line of 40 ml to the marked line of 20 ml was recorded.

In the chromatography column, 10 ml of brine was left, 0.2±0.0005 g of a sieved (30#~50#) super absorbent polymer sample was put, and brine was added to the volume of 50 ml, and then, it was allowed to stand for 30 minutes. Thereafter, a piston with weight (0.3 psi=106.26 g) was put in the chromatography column, and allowed to stand for 1 minute, and then, the lower valve of the chromatography column was opened, and a time (T1) taken until the liquid level decreased from the marked line of 40 ml to the marked line of 20 ml was recorded, thus calculating a time of T1−B (unit: second).

(4) Vortex Time

A vortex time was measured in the unit of seconds according to the method described in International Patent Publication No. 1987-003208.

Specifically, into 50 mL of a saline solution of 23° C. to 24° C., 2 g of super absorbent polymer was introduced, and while stirring with a magnetic bar (diameter 8 mm, length 30 mm) at 600 rpm, a time taken until vortex disappeared was measured in the unit of seconds, thus calculating the vortex time.

(5) Extractable Contents (EC)

Extractable contents were measured according to EDANA method WSP 270.2.

(6) Tap Water Short-Term Rewet Under No Pressure (1 Hr)

① In a cup (upper part diameter 7 cm, lower part diameter 5 cm, height 8 cm, volume 192 ml), 1 g of super absorbent polymer was put, and 100 g of tap water was poured to swell the super absorbent polymer.

② minutes after pouring tap water, the cup containing swollen super absorbent polymer was turned over on 5 pieces of filter papers (manufacturing company: whatman, catalog No. 1004-110, pore size 20-25 μm, diameter 11 cm).

③ 1 hour after pouring tap water, the cup and the super absorbent polymer were removed, and the amount of tap water (unit: g) wetted on the filter papers was measured.

(7) Tap Water Long Term Rewet Under Pressure (2 Hrs)

① In a petri dish having a diameter of 13 cm, 4 g of super absorbent polymer was uniformly sprayed and distributed, and 200 g of tap water was poured to swell the super absorbent polymer for 2 hours.

② The super absorbent polymer swollen for 2 hours was pressurized with a weight of 5 kg (0.75 psi) having a diameter of 11 cm for 1 minute on 20 pieces of filter papers (manufacturing company: whatman, catalog No. 1004-110, pore size 20-25 μm, diameter 11 cm).

③ After pressurizing for 1 minute, the amount of tap water (unit: g) wetted on the filter papers was measured.

(8) Measurement of the Content of Hydrophobic Material in Super Absorbent Polymer ④ Preparation of a standard solution of hydrophobic material 1) 0.05 g of each hydrophobic material used in Examples was completed dissolved in 5 mL of acetone to prepare a standard solution.

2) 0.2 μm of the 1) solution was filtered through a PVDF syringe filter, and then, analyzed with HPLC.

② Preparation of a sample solution 1) 1 g of the super absorbent polymer sample was put in a 40 mL vial, 1 mL of ultrapure water was put therein, and then, the super absorbent polymer was sufficiently swollen.

2) To the solution of 1), 1 mL of methanol was added, and the solution was left, and after 1 hour, 1 mL of methanol was added again.

3) To the sample of 2), 5 mL of methylene chloride was added, and the solution was shaken for 1 hour, and then, hydrophobic material was extracted.

4) The sample of 3) was centrifuged at 3500 rpm for 15 minutes, and then, 5 mL of supernatant was taken and the solvent was dried with $N_2$ blow.

5) The dried sample was dissolved in 1 mL of acetone, filtered through a 0.2 μm PVDF syringe filter, and analyzed by HPLC/CAD.

③ By analysis under the following conditions, the content of hydrophobic material in the super absorbent polymer (unit: wt %) was measured.

mobile phase
    mobile phase A: 1000 mL of acetonitrile was filtered with solvent clarification system to remove foreign substances.
    mobile phase B: 1000 mL of ultrapure water was filtered with solvent clarification system to remove foreign substances.

HPLC analysis conditions
    Column: Capcellpak C18 (4.6 mm I.D.×50 mm L., 3 μm, Shiseido)
    Eluent: mobile phase A/mobile phase B=75/25 (v/v, %)
    Flow rate: 1 mL/min
    Column temp.: 40° C.
    Run time: 15 min
    Injection Volume: 10 μl CAD analysis conditions
    Gas pressure=33.7 psi, Corona=normal
    Total flow=1.14 mL/min, Flow ratio=0.48
    Measurement was conducted in the range of 100 pA, and then, the range was controlled according to the content.

(The size of peak increases in the order of 100 pA->50 pA->20 pA).

The property values of Examples and Comparative Examples were summarized in the following Table 2.

TABLE 2

| | thickness of the polymerization sheet (mm) | Base resin (before surface treatment) | | Super absorbent polymer (after surface treatment) | | | | | | |
|---|---|---|---|---|---|---|---|---|---|---|
| | | CRC (g/g) | Vortex (sec) | CRC (g/g) | EC (wt %) | Tap water short-term rewet under no pressure (1 hr) (g) | Tap water long term rewet under pressure (2 hrs) (g) | Vortex (sec) | 0.3 psi AUP (g/g) | Permeability (sec) | the content of hydrophobic material (wt %) |
| Example 1 | 25 | 34.1 | 49 | 32.2 | 7.1 | 0.7 | 0.4 | 33 | 28.3 | 31 | 0.018 |
| Example 2 | 25 | 34.1 | 49 | 31.9 | 6.8 | 0.7 | 0.6 | 31 | 28.1 | 32 | 0.015 |
| Example 3 | 25 | 34.1 | 49 | 31.8 | 6.7 | 0.6 | 0.5 | 34 | 29.1 | 29 | 0.020 |
| Example 4 | 26 | 34.1 | 49 | 31.7 | 7.2 | 0.6 | 0.5 | 35 | 28.8 | 21 | 0.018 |
| Example 5 | 25 | 34.1 | 49 | 31.5 | 7.3 | 0.7 | 0.4 | 31 | 28.3 | 28 | 0.017 |
| Example 6 | 26 | 34.1 | 49 | 32.6 | 6.6 | 0.7 | 0.6 | 33 | 28.6 | 25 | 0.015 |

TABLE 2-continued

| | thickness of the polymerization sheet (mm) | Base resin (before surface treatment) | | Super absorbent polymer (after surface treatment) | | | | | | | |
|---|---|---|---|---|---|---|---|---|---|---|---|
| | | CRC (g/g) | Vortex (sec) | CRC (g/g) | EC (wt %) | Tap water short-term rewet under no pressure (1 hr) (g) | Tap water long term rewet under pressure (2 hrs) (g) | Vortex (sec) | 0.3 psi AUP (g/g) | Permeability (sec) | the content of hydrophobic material (wt %) |
| Example 7 | 27 | 34.1 | 49 | 31.9 | 6.7 | 0.6 | 0.5 | 32 | 28.1 | 25 | 0.016 |
| Example 8 | 26 | 34.1 | 49 | 31.7 | 7.2 | 0.7 | 0.5 | 33 | 28.9 | 24 | 0.015 |
| Example 9 | 25 | 34.1 | 49 | 32.1 | 7.1 | 0.7 | 0.4 | 33 | 28.6 | 31 | 0.017 |
| Example 10 | 26 | 34.1 | 49 | 32.4 | 6.9 | 0.6 | 0.5 | 32 | 28.5 | 33 | 0.019 |
| Example 11 | 27 | 34.1 | 49 | 32.1 | 7.0 | 0.7 | 0.5 | 31 | 29.2 | 21 | 0.018 |
| Example 12 | 26 | 34.1 | 49 | 31.7 | 7.9 | 0.9 | 0.7 | 33 | 28.1 | 27 | 0.022 |
| Example 13 | 26 | 34.1 | 49 | 31.8 | 6.9 | 0.8 | 0.7 | 32 | 27.5 | 35 | 0.019 |
| Example 14 | 27 | 34.1 | 49 | 31.9 | 7.0 | 0.8 | 0.9 | 32 | 27.9 | 30 | 0.008 |
| Example 15 | 25 | 34.1 | 49 | 32.1 | 6.7 | 0.5 | 0.3 | 31 | 28.5 | 25 | 0.035 |
| Example 16 | 26 | 34.7 | 47 | 31.8 | 5.7 | 0.5 | 0.3 | 30 | 28.5 | 30 | 0.017 |
| Example 17 | 27 | 34.1 | 49 | 32.5 | 4.8 | 0.4 | 0.3 | 29 | 29.3 | 29 | 0.020 |
| Example 18 | 25 | 34.1 | 49 | 31.9 | 7.3 | 0.6 | 0.3 | 31 | 28.1 | 33 | 0.019 |
| Example 19 | 26 | 34.1 | 49 | 31.5 | 6.8 | 0.6 | 0.3 | 31 | 28.5 | 21 | 0.017 |
| Example 20 | 27 | 33.9 | 45 | 31.1 | 6.9 | 0.4 | 0.4 | 31 | 28.6 | 29 | 0.017 |
| Example 21 | 26 | 33.3 | 41 | 30.6 | 6.3 | 0.4 | 0.3 | 29 | 28.7 | 27 | 0.018 |
| Example 22 | 27 | 33.9 | 47 | 31.3 | 6.8 | 0.5 | 0.3 | 30 | 28.6 | 27 | 0.017 |
| Com. Example 1 | 27 | 33.9 | 46 | 32.7 | 10.9 | 3.1 | 3.5 | 33 | 28.1 | 41 | Not detected |
| Com. Example 2 | 27 | 34.9 | 46 | 29.8 | 12.1 | 4.2 | 4.7 | 34 | 26.4 | 42 | 0.017 |
| Com. Example 3 | 26 | 34.9 | 46 | 29.1 | 11.6 | 4.8 | 5.4 | 35 | 26.4 | 46 | 0.019 |
| Com. Example 4 | 26 | 34.5 | 45 | 31.9 | 11.6 | 4.3 | 6.1 | 33 | 26.7 | 44 | 0.015 |
| Com. Example 5 | 26 | 35.5 | 55 | 33.5 | 7.0 | 1.6 | 1.1 | 40 | 27.6 | 30 | 0.018 |
| Com. Example 6 | 15 | 33.5 | 45 | 31.3 | 9.6 | 2.1 | 1.7 | 33 | 27.8 | 31 | 0.017 |
| Com. Example 7 | 4 | 33.0 | 45 | 31.1 | 10.1 | 1.9 | 2.1 | 34 | 28.1 | 31 | 0.019 |

Referring to Table 2, it was confirmed that Examples of the present invention exhibited excellent vortex time and permeability, and very low tap water rewet amounts under no pressure and under pressure, thus exhibiting improved rewet property.

To the contrary, it can be seen that in Comparative Examples 1 to 7, rewet property and permeability are inferior to Examples.

Particularly, in case the content of the first internal cross-linking agent was too small as in Comparative Example 5, vortex was not good.

In the case of Comparative Examples 6 and 7 wherein the content rate of the first internal cross-linking agent to the second internal cross-linking agent does not fall within a predetermined range, and the first internal cross-linking agent is excessively used, it was confirmed that volume expansion excessively occurred during polymerization, and thus, the thickness of the super absorbent polymer resin sheet became thin after polymerization, and the polymerization process became unstable.

What is claimed is:

1. A super absorbent polymer comprising:
   base resin particles in which acrylic acid-based monomers having acid groups, of which at least a part is neutralized, and an internal cross-linking agent are cross-linked in the form of a cross-linked polymer;
   a surface modification layer formed on a surface of the base resin particles, in which the cross-linked polymer is additionally cross-linked by an epoxy-based surface cross-linking agent; and
   an inorganic filler,
   wherein the internal cross-linking agent comprises a poly(meth)acrylate-based first internal cross-linking agent and a polyol polyglycidyl ether-based second internal cross-linking agent at a weight ratio of the first internal cross-linking agent to the second internal cross-linking agent of 1:40 to 1:1200, and
   the surface modification layer includes a hydrophobic material having a melting temperature (Tm) of 40 to 80° C., and a water solubility at 25° C. of 70 mg/L or less.

2. The super absorbent polymer according to claim 1, wherein the first internal cross-linking agent includes one or more of trimethylolpropane tri(meth)acrylate, ethyleneglycol di(meth)acrylate, polyethyleneglycol di(meth)acrylate, propyleneglycol di(meth)acrylate, polypropyleneglycol di(meth)acrylate, butanediol di(meth)acrylate, diethyleneglycol di(meth)acrylate, hexanediol di(meth)acrylate, triethyleneglycol di(meth)acrylate, tripropyleneglycol di(meth)acrylate, tetraethyleneglycol di(meth)acrylate, dipentaerythritol pentaacrylate, glycerin tri(meth)acrylate, or pentaerythritol tetraacrylate.

3. The super absorbent polymer according to claim 1, wherein the second internal cross-linking agent includes one or more of ethyleneglycol diglycidyl ether, polyethyleneglycol diglycidyl ether, glycerol polyglycidyl ether, propyleneglycol diglycidyl ether, or polypropyleneglycol diglycidyl ether.

4. The super absorbent polymer according to claim 1, wherein the super absorbent polymer has extractable contents (EC) measured according to EDANA method WSP 270.2 of 9.0 wt % or less.

5. The super absorbent polymer according to claim 1, wherein the super absorbent polymer has a vortex time of 35 seconds or less.

6. The super absorbent polymer according to claim 1, wherein the super absorbent polymer has a permeability (unit: seconds) measured according to the following Equation 1, of 40 seconds or less:

Permeability (sec)=$T1-B$ [Equation 1]

in the Equation 1,

T1 is a time taken until a height of a liquid level decreases from 40 ml to 20 ml, after putting 0.2±0.0005 g of a sieved (30#~50#) super absorbent polymer sample in a chromatography column and adding brine to a volume of 50 ml, and then, leaving it for 30 minutes; and B is a time taken until a height of a liquid level decreases from 40 ml to 20 ml in a chromatography column filled with brine.

7. The super absorbent polymer according to claim 1, wherein the super absorbent polymer has a rewet property (tap water short-term rewet under no pressure) of 1.5 g or less, said rewet property being defined by a weight of water exuding from super absorbent polymer to a filter paper, after 1 g of the super absorbent polymer is soaked in 100 g of tap water to swell for 10 minutes, and then, the swollen super absorbent polymer is left on the filter paper for 1 hour from a first time when it is soaked in the tap water.

8. The super absorbent polymer according to claim 1, wherein the super absorbent polymer has a rewet property (tap water long-term rewet under pressure) of 1.5 g or less, said rewet property being defined by a weight of water exuding from super absorbent polymer to a filter paper, after 4 g of the super absorbent polymer is soaked in 200 g of tap water to swell for 2 hours, and then, the swollen super absorbent polymer is left on the filter paper for 1 minute under pressure of 0.75 psi.

9. A method for preparing super absorbent polymer comprising:
preparing a base resin in which acrylic acid-based monomers having acid groups, of which at least a part are neutralized, and an internal cross-linking agent are cross-linked;
mixing a hydrophobic material having a melting temperature (Tm) of 40 to 80° C., and a water solubility at 25° C. of 70 mg/L or less, and an epoxy-based surface cross-linking agent with the base resin to prepare a mixture; and
increasing a temperature of the mixture to conduct surface modification of the base resin,
wherein the internal cross-linking agent comprises a poly (meth)acrylate-based first internal cross-linking agent and a polyol polyglycidyl ether-based second internal cross-linking agent at a weight ratio of the first internal cross-linking agent to the second internal cross-linking agent of 1:40 to 1:1200, and
an inorganic filler is additionally mixed with the base resin in the mixture, or the inorganic filler is mixed with the super absorbent polymer as the temperature of the mixture is increased to conduct surface modification.

10. The method for preparing super absorbent polymer according to claim 9, wherein while preparing the mixture, the hydrophobic material is dry-mixed with the base resin, and then, the epoxy-based surface cross-linking agent is dissolved in water and mixed in a state of a surface cross-linking solution.

11. The method for preparing super absorbent polymer according to claim 9, wherein the hydrophobic material includes one or more of lauric acid, myristic acid, cetyl alcohol, stearic acid, glycol stearate, glycerol monostearate, glycol distearate, stearin, pentaerythrityl distearate, or oleamide.

12. The method for preparing super absorbent polymer according to claim 9, wherein the hydrophobic material is mixed in a content of 0.02 to 0.5 parts by weight, based on 100 parts by weight of the base resin.

13. The method for preparing super absorbent polymer according to claim 9, wherein the first internal cross-linking agent includes one or more of trimethylolpropane tri(meth)acrylate, ethyleneglycol di(meth)acrylate, polyethyleneglycol di(meth)acrylate, propyleneglycol di(meth)acrylate, polypropyleneglycol di(meth)acrylate, butanediol di(meth)acrylate, diethyleneglycol di(meth)acrylate, hexanediol di(meth)acrylate, triethyleneglycol di(meth)acrylate, tripropyleneglycol di(meth)acrylate, tetraethyleneglycol di(meth)acrylate, dipentaerythritol pentaacrylate, glycerin tri(meth)acrylate, or pentaerythritol tetraacrylate.

14. The method for preparing super absorbent polymer according to claim 9, wherein the second internal cross-linking agent includes one or more of ethyleneglycol diglycidyl ether, polyethyleneglycol diglycidyl ether, glycerol polyglycidyl ether, propyleneglycol diglycidyl ether, or polypropyleneglycol diglycidyl ether.

15. The method for preparing super absorbent polymer according to claim 9, wherein the epoxy-based surface cross-linking agent includes one or more of ethyleneglycol diglycidyl ether, diethyleneglycol diglycidyl ether, triethyleneglycol diglycidyl ether, tetraethyleneglycol diglycidyl ether, glycerin polyglycidyl ether, or sorbitol polyglycidyl ether.

16. The method for preparing super absorbent polymer according to claim 9, wherein the epoxy-based surface cross-linking agent is mixed in a content of 0.005 to 0.5 parts by weight, based on 100 parts by weight of the base resin.

17. The method for preparing super absorbent polymer according to claim 9, wherein the temperature of the mixture is increased to 100 to 170° C.

18. The method for preparing super absorbent polymer according to claim 9, wherein the inorganic filler includes one or more of fumed silica or precipitated silica, and
the inorganic filler is mixed in a content of 0.01 to 0.5 parts by weight, based on 100 parts by weight of the base resin or super absorbent polymer.

19. The method for preparing super absorbent polymer according to claim 9, wherein the preparing the base resin comprises:
polymerizing a monomer composition comprising acrylic acid-based monomers having acid groups, of which at least a part is neutralized, an internal crosslinking agent, and a polymerization initiator to form hydrogel polymer;
drying the hydrogel polymer;
grinding the dried polymer; and
sieving the ground polymer.

20. The method for preparing super absorbent polymer according to claim 19, wherein the monomer composition further comprises colloidal silica included in a content of 0.01 to 1.0 parts by weight, based on 100 parts by weight of the acrylic acid-based monomers.

* * * * *